United States Patent [19]

Neves

[11] 4,425,433

[45] Jan. 10, 1984

[54] ALCOHOL MANUFACTURING PROCESS

[76] Inventor: Alan M. Neves, 1596 24th St., Ogden, Utah 84401

[21] Appl. No.: 195,326

[22] Filed: Oct. 20, 1980

Related U.S. Application Data

[63] Continuation-in-part of Ser. No. 88,196, Oct. 23, 1979, abandoned.

[51] Int. Cl.$^3$ .............................................. C12P 7/08
[52] U.S. Cl. .................................. 435/163; 435/161; 435/165; 435/813
[58] Field of Search ............... 435/161, 162, 163, 165, 435/813

[56] References Cited

U.S. PATENT DOCUMENTS

| | | | |
|---|---|---|---|
| 985,726 | 2/1911 | Cohoe . | |
| 2,053,769 | 9/1936 | Dreyfus | 202/42 |
| 2,088,977 | 8/1937 | Scholler et al. | 127/1 |
| 2,222,885 | 11/1940 | Thomsen | 127/37 |
| 2,451,156 | 10/1948 | DeMattos | 195/141 |
| 2,681,871 | 6/1954 | Wallace | 137/1 |
| 2,801,939 | 8/1957 | Hignett et al. | 127/37 |
| 2,862,819 | 12/1958 | Hougen et al. | 99/49 |
| 3,212,932 | 10/1965 | Hess et al. | 127/37 |
| 3,212,933 | 10/1965 | Hess et al. | 127/37 |
| 3,234,026 | 2/1966 | Coutts | 99/31 |
| 3,585,104 | 6/1971 | Kleinert | 162/17 |
| 3,667,961 | 6/1972 | Algeo | 99/2 R |
| 3,799,845 | 3/1974 | Love | 203/99 |
| 3,930,042 | 12/1975 | Dunnet | 426/475 |
| 3,939,286 | 2/1976 | Jelks | 426/312 |
| 4,009,075 | 2/1977 | Hoge | 195/33 |
| 4,053,645 | 10/1977 | Jelks | 426/53 |
| 4,093,516 | 6/1978 | Lang | 195/27 |
| 4,094,740 | 6/1978 | Lang | 195/27 |
| 4,094,742 | 6/1978 | Bellamy | 195/33 |
| 4,125,063 | 11/1978 | Jelks | 99/471 |
| 4,136,207 | 1/1979 | Bender | 426/510 |

OTHER PUBLICATIONS

Gene Bylinsky, "Biomass: The Self-Replacing Energy Resource," *Fortune* 78-81, (Sep. 24, 1979).

William B. Altsheler et al., "Design of a Two-Bushel Per Day Continuous Alcohol Unit," 43 *Chemical Engineering Progress*, 467-72, (Sep. 1947).

William C. Mann, "Biomass Refinery Turns Crop Wastes Into Fuel," *Popular Science*, 78-80, (Apr. 1979).

George T. Tsao, "Cellulosic Material as a Renewable Resource," *Process Biochemistry*, 12-14, (Oct. 1978).

H. R. Bilford et al., "Preliminary Report on Fast, Continuous Fermentation," *Food For Thought*, 173-209, (1942).

*Energy Primer: Solar, Water, Wind, and Biofuels*, 208-13, (R. Merrill et al., ed., 1978).

*Primary Examiner*—R. B. Penland
*Attorney, Agent, or Firm*—H. Ross Workman; Allen R. Jensen; Dale E. Hulse

[57] ABSTRACT

A continuous process for the production of alcohol, preferably ethanol, from cellulosic materials. The cellulosic materials are delignified such that the hemicellulose and the cellulose can be subsequently acid hydrolyzed into simple sugars. These sugars are fermented in the presence of yeast to yield ethanol and carbon dioxide. The alcohol vapor is removed from the fermentation solution under a reduced pressure and subsequently distilled. Carbon dioxide gas may be sparged throughout the fermenting solution in order to aid in the removal of the alcohol from the fermenting solution. The gaseous carbon dioxide is captured and utilized in the manufacture of additional quantities of ethanol or other basic chemicals.

29 Claims, 6 Drawing Figures

ALCOHOL MANUFACTURING PROCESS

RELATED APPLICATION

This application is a continuation-in-part of my co-pending United States patent application Ser. No. 088,196 which was filed Oct. 23, 1979, now abandoned.

BACKGROUND

1. Field of the Invention

The present invention relates to the manufacture of alcohol. More particularly, it relates to a process for the continuous production of ethanol.

2. The Prior Art

In light of the steadily increasing demand for liquid fuels and the shrinking resources for petroleum crude oil, researchers have begun to investigate alternative liquid fuels to determine the feasibility of commercially producing such substitutes in order to fulfill this increasing demand. Recent world events, including the shortage of petroleum crude oil, the sharp increase in the cost of oil and gasoline products, and the political instability of many oil-producing countries, have demonstrated the vulnerability of the present sources of liquid fuels. Even if such supply and economic instabilities were acceptable, it is clear that the worldwide production of petroleum products at forecasted levels can neither keep pace with the increasing demand nor continue indefinitely. It is becoming evident that the time will soon come when there will have to be a transition to resources which are plentiful and preferably renewable.

One of the most generally recognized substitutes which could be made available in significant quantities in the near future is alcohol, and in particular, ethanol. See "The Report of the Alcohol Fuels Policy Review" (Dept. of Energy/PE-0012, June 1979). For example, there are currently many outlets in the United States and throughout the world which sell a blend of gasoline and about 10 percent to 20 percent ethanol (commonly called "gasohol") which can be used as a fuel in conventional automobile engines. Furthermore, ethanol can be blended with additives to produce a liquid ethanol-based fuel (that is, ethanol is the major component) which is suitable for operation in most types of engines. Such an ethanol-based fuel is disclosed in copending United States application Ser. No. 087,618 filed on Oct. 23, 1979. It is to the problem of how to produce sufficient quantities of ethanol needed for use in such substitute fuels in order to meet the increased demand for liquid fuels that the present invention is directed.

It is well-known that ethanol can be produced by fermentation. Even today, throughout most of the world, ethanol is produced through the fermentation process. In the United States, however, only about 25 percent of the total production of ethanol is by fermentation, the remaining portion being synthetically produced, generally from ethylene.

In the fermentation process, yeast is added to a solution of simple sugars. Yeast is a small microorganism which uses the sugar in the solution as food, and in doing so, expels ethanol and carbon dioxide as by-products. The carbon dioxide comes off as a gas, bubbling up through the liquid, and the ethanol stays in solution. Unfortunately, the yeast stagnate when the concentration of the ethanol in solution approaches about 18 percent by volume, whether or not there are still fermentable sugars present.

Accordingly, in order for nearly complete fermentation, and in order to produce large quantities of ethanol, the common practice has been to use a batch process wherein extremely large fermentation vessels capable of holding upwards of 500,000 gallons are used. With such large vessels, it is economically unrealistic to provide an amount of yeast sufficient to rapidly ferment the sugar solution. Hence, conventional fermentation processes have required 72 hours and more because such time periods are required for the yeast population to build to the necessary concentration. For example, a quantity of yeast is added to the fermentation vessel. In approximately 45–60 minutes, the yeast population will have doubled; in another 45–60 minutes that new yeast population will have doubled. It takes many hours of such propogation to produce the quantity of yeast necessary to ferment such a large quantity of sugar solution.

Furtermore, the sugars used in such traditional fermentation processes had typically contained from about 6 percent to 20 percent of the larger, complex sugars (such as dextrins and dextrose) which take a much longer time to undergo fermentation, if they will undergo fermentation, than do the simple hexose sugars (such as glucose and fructose). Thus, it is common practice to terminate the fermentation process after a specified period, such as 72 hours, even though not all of the sugars have been utilized. Viewing the prior art processes from an economic standpoint, it is preferable to sacrifice the remaining unfermented sugars than to wait for the complete fermentation of all of the sugars in the batch.

In addition, experience has taught that it is preferable to add malt enzymes which aid in the hydrolysis of starches and conversion of the higher complex dextrin and dextrose sugars which are present in the sugar solutions of the prior art fermentation processes. While such malt enzymes add a desirable flavor to ethanol produced for human consumption, the malt enzymes do nothing to make ethanol a more advantageous liquid fuel substitute and, in fact, could create problems for such a use.

One of the important concerns with conventional fermentation systems is the difficulty of maintaining a sterile condition free from bacteria in the large-sized batches and with the long fermentation period. Unfortunately, the optimum atmosphere for fermentation is also extremely condusive to bacterial growth. Should a batch become contaminated, not only must the yeast and sugar solution be discarded, but the entire fermentation vessel must be emptied, cleaned, and sterilized. Such an occurrance is both time-consuming and very costly.

After fermentation, traditional processes have removed the ethanol from the fermentation solution and further concentrated the ethanol product by distillation. Distillation towers capable of such separation and concentration are well-known in the art.

From the foregoing, it is clear that the form of the sugars used in the fermentation process is important to the efficiency of production and the yield of ethanol. It is highly desirable that sugars used in the fermentation process preferably be the simple hexose sugars so that the fermentation period is minimized and as much as possible of the sugar can be utilized in the fermentation process, thereby resulting in a higher yield of ethanol.

Prior art ethanol fermentation processes have generally been restricted to the use of small grains as the source of the fermentable sugars. These grains are particularly advantageous because the starch therein is readily hydrolyzed to sugars. Unfortunately, while most of the resulting sugars are fermentable, typically 6 percent to 20 percent of the sugars are the slow fermenting or nonfermenting complex sugars. Moreover, to obtain the fermentable sugars from such grain sources is extremely expensive. Thus, if large quantities of ethanol are to be produced for use as a substitute liquid fuel at a reasonable cost, other sources must be considered for obtaining the fermentable sugars. Although it has been shown under laboratory conditions that such sugars can be obtained from cellulose-containing materials, the hydrolysis process for releasing the fermentable sugar is known to be very difficult. Hence, researchers in the past have not found an economically acceptable method for manufacturing ethanol from such cellulosic sources.

BRIEF SUMMARY AND OBJECTS OF THE INVENTION

The present invention is directed to a continuous method of manufacturing alcohol, preferably ethanol, which is suitable for use as a liquid fuel, from cellulose-containing materials.

The process of the present invention preferably begins with cellulose-containing materials, including materials which are typically considered as wastes. The cellulosic materials are prepared by chopping, grinding, and/or milling processes which reduce the cellulosic material to a powdered feedstock.

This feedstock undergoes a delignification process which separates the three major components of the cellulosic source materials: cellulose, hemicellulose, and lignin. First, the feedstock is mixed with a dilute acid solution and heated to an elevated temperature at a slight pressure for a short period of time. After the acid is neutralized, easily digestible starches and sugars and the hemicellulose remain in solution, while the lignin and cellulose are filtrable solids. The hemicellulose solution is ready to be hydrolyzed to simple sugars.

According to the present invention, there are alternative processes for separating the lignin and cellulose solids. Utilizing the first process, the lignin and cellulose solids are mixed with a moderate concentration of cadoxen (a highly basic solvent) and then heated to an elevated temperature and a slight pressure for a relatively short period of time. According to the second process, the lignin and cellulose solids are chilled and reacted with a chilled, highly concentrated acid for a relatively short period of time. With either the cadoxen or the acid process, the resultant solution contains the cellulose, while the lignin remains as filtrable solids. When the cadoxen process is used, the cellulose is precipitated as a soft floc by cooling and aqueous dilution; when the acid process is used, the cellulose is precipitated as a soft floc by the addition of methanol. The soft floc cellulose and the previously separated hemicellulose solution are combined prior to hydrolyzation.

By the third alternative and presently preferred process, the lignin and cellulose solids are heated under high pressure in the presence of steam to a temperature in excess of about 400° F. for a short period of time. The solids are then ejected into a flash chamber which is maintained at about atmospheric pressure. The resulting material is combined with the previously separated hemicellulose solution prior to hydrolyzation.

The hydrolyzation process is conducted in a relatively dilute acid solution at an elevated temperature under pressure for a short period. The subsequently obtained solution is neutralized to a pH of about 4.5 to 5.0, and the lignin solids are separated. The resultant slurry or "wort" contains essentially only simple hexose sugars, as opposed to the larger complex sugars. As the wort is cooled to about 88° F. to 90° F. (the preferable fermentation temperature), yeast nutrients are added. The wort is then pumped into a continuous fermentation vessel where it can be almost completely fermented in a period as short as about 3 to 6 hours—a period significantly less than the prior art processes requiring 72 hours.

The present invention also includes alternative methods for fermenting the wort to ethanol and then purifying the ethanol. Using the first method, the liquid in the top of the fermentation vessel, which contains a high concentration of ethanol, is allowed to enter a secondary fermentation tank where fermentation continues for a few more hours in order to convert essentially all of the sugars to ethanol. The resultant solution, called "wash", is heated to a high temperature and then distilled under low pressure. This high temperature, low pressure distillation results in a high degree of separation of the ethanol in only a single distillation. The resultant ethanol distillate can then undergo final processing where it may be dehydrated, denatured, stored, and/or blended with other components into a motor fuel.

Alternatively, carbon dioxide, which is a significant byproduct of the fermentation process, is sparged throughout the wort in the fermentation vessel. By pulling a vacuum on the top of the fermentation vessel, the carbon dioxide will carry the ethanol from the fermentation solution. The ethanol can be easily obtained by cooling the carbon dioxide-ethanol vapor and collecting the ethanol condensate. The ethanol can then be finally processed.

A still further alternative method uses the sparging carbon dioxide technique to remove ethanol from the fermentation vessel under reduced pressure and then the vaporized ethanol is put through a distillation tower under reduced pressure so that a legally anhydrous ethanol product is obtained without the use of complicated distillation techniques.

It is also within the scope of the present invention to capture the carbon dioxide which is released from the fermentation process and utilize it to make other important chemicals such as acetylene, benzene, and methanol. Moreover, the carbon dioxide can be synthetically converted to produce even additional amounts of ethanol.

It is, therefore, an object of the present invention to provide for a continuous method of manufacturing ethanol in a minimal amount of time and at high yields.

It is another object of the present invention to provide for an ethanol manufacturing process which is capable of utilizing many types of cellulosic wastes in the fermentation process.

It is still another object of the present invention to utilize the carbon dioxide which is expelled in the fermentation process in the manufacture of other chemical products.

It is a further object of the present invention to provide an ethanol product at a reasonable cost.

These and other objects and features of the present invention will become more fully apparent from the following description and appended claims taken in conjunction with the accompanying drawings.

DETAILED DESCRIPTION OF THE PREFERRED EMBODIMENT

Figure 1:
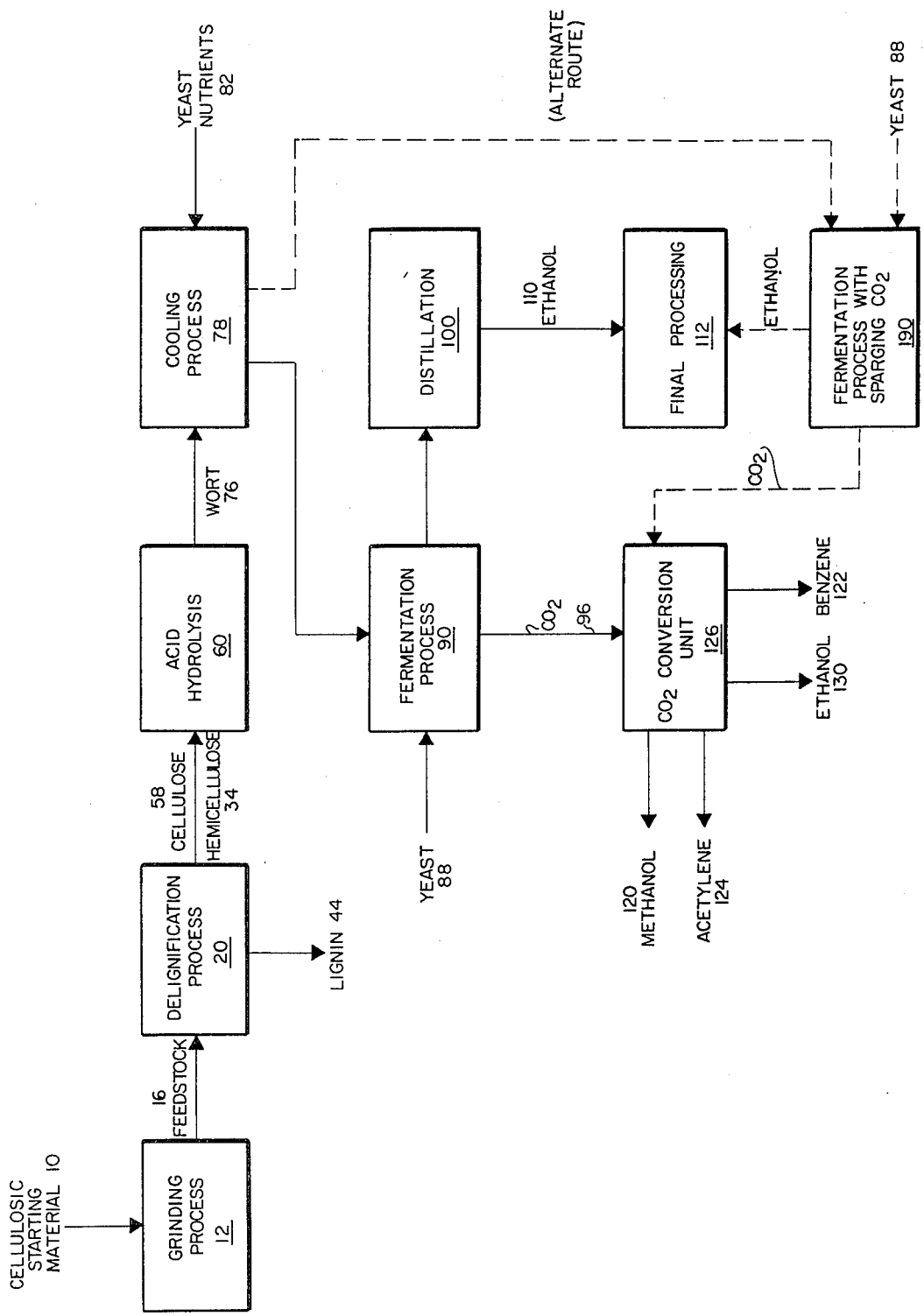
FIG. 1 is a block diagram representation of the ethanol manufacturing process of the present invention.

The present invention relates to a method of manufacturing alcohol in a continuous manufacturing process which uses cellulose-containing wastes as the starting materials. It has been found that cellulosic materials often considered as wastes can be utilized in the ethanol manufacturing process of the present invention to produce ethanol in a better yield and at a significantly reduced cost, as compared with the prior art processes. It will be recognized that any starch-containing material (such as barley, corn, rice, wheat, and other small grains) in which the starch can be readily converted to simple sugars, as well as any sugar-containing material (such as sugar beets or sugar cane) may be used according to the disclosed process. Nevertheless, it is not necessary nor is it economically desirable to limit the use of the present invention to such expensive starch or sugar-containing materials.

In general, most cellulosic materials contain three major components: cellulose, hemicellulose, and lignin, in the approximate ratios of 4:3:3, respectively. However, these are only approximations; for example, softwood contains a typical ratio of 42:25:28, corncobs contain proportions of about 40:36:13 with an additional 8 percent simple sugars, whereas city garbage contains about 75 to 90 percent cellulose.

Cellulose is a homogenous polymer of anhydroglucose units linked together by 1,4-beta-glucosidic linkages, as compared to the 1,4 and 1,6 alpha-linkages of starch. Hemicellulose is a mixture of simple or mixed polysaccharides, including polymers of pentoses (such as xylose and arabinose), hexoses (such as mannose, galactose and glucose), and sugar acid. Lignin is a branched polymer macromolecule having three-dimensional randomly linked polyphenolic units. The general aromatic character of lignin, as well as the prevelance of covalent carbon bonds, prevents reversion to monomers during processing lignin and cellulose from the "woody" fibrous cell walls of plants and is the cementing material between adjacent cell walls.

Although it is relatively simple to hydrolyze hemicellulose to simple sugars, cellulose is strongly hydrolysis resistant because (1) cellulose is a highly ordered crystalline structure and (2) lignin physically surrounds and seals the cellulose. The difficulty in using cellulose in the manufacturing of ethanol is the necessity to free the cellulose molecules from the lignin seal and the crystalline structure, but once this is done, the 1,4-beta-glucosidic linkages in cellulose are no more difficult to hydrolyze than the 1,4-alpha-glucosidic linkages in starch.

In view of the fact that nearly any cellulose-containing material may be a starting material for the present invention, many materials heretofore considered only as wastes may be utilized. Recent statistics demonstrate the plentiful availability of such cellulosic waste resources, as compared to traditional petroleum and ethanol resources:

|  | Tons/Year ($\times$ $10^6$) |
|---|---|
| Petroleum crude oil (annual consumption) | 820 |
| Grains | 355 |
| Cellulosic wastes: | 1,010 |
| Corn residue | 140 ($\times$ $10^6$) |
| Forestry | 200 |
| Feedlot | 237 |
| Bagasse | 10 |
| Other cropwastes | 233 |
| Urban | 130 |
| Industrial | 60 |

By utilizing such heretofore untapped cellulosic waste materials as the source material for the process of the present invention, the possibility of providing vast amounts of ethanol without the necessity of substantially increasing the production of expensive starch-containing grains is created. Furthermore, unlike petroleum crude oil, most cellulosic waste materials are annually renewable.

If urban or industrial wastes are used as the starting materials, it is first necessary to sort the cellulosic materials. This may be accomplished in any convenient manner. For example, Teledyne National Corporation markets a series of machines capable of various sorting, shredding, drying, and compressing operations which reduce the cellulosic material from the wastes to a pelletized form. The pelletized cellulosic material can be easily ground to the necessary size.

Figure 2:
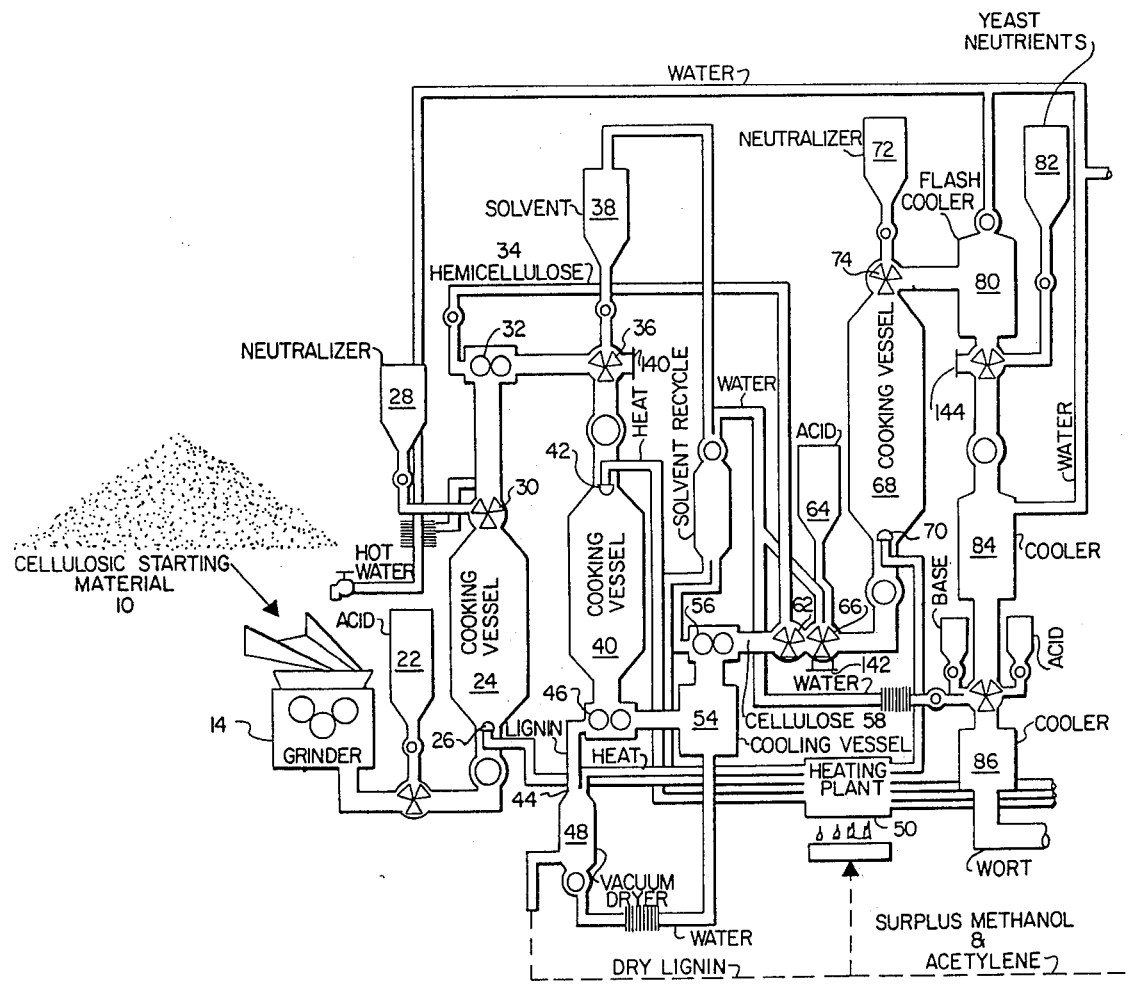
FIG. 2 is a schematic representation of an embodiment of that portion of the continuous manufacturing process of the present invention in which the cellulosic materials are converted into simple sugars in preparation for the fermentation process.

With reference to FIGS. 1 and 2, the cellulosic starting materials 10 are subjected to chopping, grinding, and milling operations in order to reduce the starting materials to a workable size. These operations are generally designated as grinding process 12. It has been found preferable to grind the raw cellulosic material into a feedstock of very small size in order that the cellulosic material can be easily delignified. It has been found best if the feedstock has an average particle size of not greater than about $\frac{1}{8}$ inch. Preferably, the feedstock should be small enough that when diluted, it will pass through about a 20 mesh screen. If readily hydrolyzable starch or sugar-containing materials, such as grains or sugar beets, are used, the average size of the feedstock materials need not be so small. From an economical viewpoint, wet grinders, such as represented as grinder 14 in FIG. 2, have been found to be more efficient and to use less energy than dry grinders. Furthermore, the use of hot water (near its boiling point) has been found to aid the grinding process.

The resulting feedstock 16 is next subjected to a delignification process 20 in which the three major components of the feedstock (cellulose, hemicellulose, and lignin) are separated. In the initial step of the delignification process, the hemicellulose along with the easily digestable starches and sugars are removed. Feedstock 16 is diluted with water, combined with dilute acid 22 and heated in cooking vessel 24 at an elevated temperature under slight pressure. Although acid 22, which is preferably sulfuric acid, may be added in concentrations upwards of 20 percent by volume, concentrations in the range of about 0.5 percent to 2.0 percent have been found to be generally sufficient. In fact, such lower concentrations are preferable so that the action of the hydrogen ion is limited, that is, the concentration of the hydrogen ion is not high enough to hydrolyze the hemicellulose. Although this step of the delignification process may be performed over a broad range of temperatures and pressures, it has been found desirable to heat the feedstock at a temperature of about 200° F. to 300° F. at a pressure of about 5 psi to 50 psi for about 2 to 10 minutes under conditions of agitation. (Unless otherwise stated, all pressure measurements are given in terms relative to the atmosphere and not in terms of absolute pressures.) The presently preferred conditions are a temperature of about 225° F. at a pressure of about 15 psi for about 3 to 6 minutes.

In the continuous manufacturing process, it is, therfore, preferable to mix acid 22 with feedstock 16 and then continuously pump the resulting acidic feedstock solution into one end of cooking vessel 24. Agitation is provided within vessel 24, and the feedstock solution is withdrawn from the other end of the vessel after an approximate residency time. It has also been found preferable in such a continuous manufacturing process to use a cooking vessel that is capable of instantly heating the feedstock solution to the cooking temperature. This can be easily accomplished by using a jet heater 26 which sparges steam throughout the feedstock solution as it enters the cooking vessel. Of course, other types of heaters (such as heaters utilizing steam coils) may be used.

At this point, neutralizer 28 may be added at 30 to the acidic feedstock solution as it is removed from cooking vessel 24 until a pH of about 4.0 to 6.0 is obtained. If the acidic feedstock is neutralized, the preferable neutralizers are sodium carbonate or sodium bicarbonate. Separator 32 filters the resultant solution (containing the readily digestible starches, sugars, and hemicellulose 34), from the solids (containing the cellulose and lignin). Hemicellulose 34 is then ready for the acid hydrolysis process of cooking vessel 68, which is discussed in detail hereinafter. Hemicellulose 34 may be combined at 62 with the cellulose (after the cellulose has been delignified) prior to hydrolysis or it may be hydrolyzed and then fermented separately. Since the hemicellulose-containing solution is to be reacidified during the subsequent hydrolysis step and since neutralization is not generally necessary in order for the hemicellulose to dissolve into solution, it has been found that the neutralization step can generally be omitted.

The solids separated from the hemicellulose solution are next processed to separate the lignin from the cellulose. This may be accomplished by alternative methods. According to the first method, which is represented in FIG. 2, the solids are diluted with water and mixed at 36 with a cadoxen solvent 38 (ethylene diamine cation in an aqueous concentration of about 25 percent by volume) to an amount of about 10 percent to 20 percent by volume of water. The resulting solution is pumped into cooking vessel 40, preferably designed so that the solution entering the vessel is instantaneously heated by jet heater 42. The solution in cooking vessel 40 is heated to an elevated temperature of from about 150° F. to 240° F. and a pressure from about atmospheric pressure to about 15 psi for about 2 to 10 minutes under conditions of agitation. Such conditions have been found to be sufficient to break up the lignin seal surrounding the cellulose and break down the high order cellulose structure such that the cellulose will dissolve into solution. It will be appreciated that a longer residency time or a higher temperature and pressure may be needed depending on the particular starting cellulosic material used, how lightly the cellulose is bonded by the lignin, or the size to which the cellulosic starting materials had been ground. The presently preferred conditions are at a temperature of about 200° F. at atmospheric pressure for about 3 to 6 minutes.

The undissolved solids containing mostly lignin 44 may be filtered from the cellulose-containing solution by separator 46. These lignin solids 44 may be dried, such as by vacuum dryer 48, and then used as a fuel for the heating plant 50, which supplies heat to the entire manufacturing operation. Recycling of the byproducts, such as using the lignin, can be a significant factor in the economic feasibility of the ethanol manufacturing process of the present invention.

It will be appreciated that the lignin need not be separated from the cellulose solution at this point in the process since the lignin is not subject to degradation in the subsequent hydrolysis process. For example, in a given particular processing facility, it may be easier to accomplish this lignin separation after hydrolyzation of the cellulose; such a filtration could easily be accomplished after the mixture had been cooled in cooler 86. At this point in the process, the mixture would not be strongly acid nor would it be strongly basic. The presence of the strong acids or bases used in the delignification process can cause maintenance problems in separator 46.

The cellulose-containing cadoxen solution is then cooled in cooling vessel 54 and diluted with water. As solution 52 cools, the cellulose precipitates as a soft floc which can be filtered from the cadoxen solvent by separator 56. Cadoxen solvent 38 may then be recycled, as indicated in FIG. 2. This soft floc cellulose 58 must be quickly subjected to acid hydrolysis; otherwise, the soft floc will harden and become resistant to acid hydrolysis. That it is necessary to quickly hydrolyze the soft floc soon after it forms is a significant reason why those skilled in the prior art have not heretofore been able to use cellulosic starting materials in the batch processes of the prior art.

As an alternative to the cadoxen treatment for delignification of the cellulose, concentrated sulfuric acid may be used. With such a treatment process, sulfuric acid in concentrations of about 60 percent to 90 percent by weight, and preferably of about 72 percent to 75 percent, is added to the lignin and cellulose solids which are filtered from the hemicellulose solution by separator 32. Other acids may be used. For example, hydrochloric acid in concentrations of about 30 percent to about 60 percent, preferably about 40 percent, has been found to effectively delignify the cellulosic material.

The solids and concentrated acid may be cooked at a temperature of from about 150° F. to 240° F. for about 2 to 10 minutes, (preferably at a temperature of about 200° F. for a period of about 3 to 6 minutes). When the resultant solution is cooled and diluted with methanol, the cellulose will precipitate as a soft floc.

Unfortunately, it has been found that when the lignin and cellulose solids are heated above room temperature in concentrated sulfuric acid, the resultant material often is a black tar-like substance. The presence of this tar-like substance greatly complicates the reprecipitation of the cellulose floc prior to the hydrolysis process. When the lignin and cellulose solids are reacted with the concentrated sulfuric acid at a temperature of about 60° F. to 75° F., the result is a gray colloidal solution in which some of the cellulose has been charred and some of the sugars have undergone degradation. Again, the collodial material complicates the reprecipitation of the cellulose floc.

It has been discovered that substantial charring of the cellulose and degradation of the sugars can be avoided by chilling the concentrated sulfuric acid and the cellulose and lignin solids to a temperature of about 30° F. to 60° F. (the preferable temperature is about 40° F. to 50° F.) and then allowing the reaction to proceed with vigorous agitation for about 1 to 10 minutes. The high acid concentration at such cool temperatures is still capable of breaking down the lignin and cellulose structures and dissolving the cellulose. And in addition, the cool temperatures slow the degradation of the cellulose by minimizing the formation of hydrogen ion which would begin to hydrolyze the cellulose into cellibose which is not fermentable. Under these temperature conditions, most of the cellulose will dissolve in the concentrated acid. The resultant acid solution, when diluted with methanol, will yield a soft floc precipitate of cellulose 58. Utilizing this method of delignification, cooking vessel 40 (shown in FIG. 2) would be replaced by a cooling vessel in which the temperature of the reactants could be lowered to the desired temperature. This cellulose precipitate 58 can be separated and hydrolyzed as if the cadoxen treatment were used. Of course, the acid and methanol are preferably recycled.

In preparation for the acid hydrolysis process, cellulose 58 (in the form of a soft floc) is diluted with water for convenience in handling and mixed at 62 with hemicellulose 34. This slurry is then mixed with acid 64, preferably sulfuric acid, to obtain a concentration by volume of water of about 0.5 percent to 10 percent. It has been found that this mixing is best accomplished in a continuous slurry mixing tank 66, so that there is a complete mixing of the components. The slurry is heated in cooking vessel 68, preferably instantaneously by jet-heater 70, to a temperature of about 200° F. to 400° F. at a pressure of about 15 psi to 200 psi for a period of about 2 to 10 minutes. It will be appreciated that the temperature, pressure, and residency time are interdependent so that the modifications in any may be made in order to accommodate the acid hydrolysis process into the continuous manufacturing process. For example, if easily hydrolyzable starches are used, a temperature of about 200° F. at 15 psi will be sufficient. However, if more hydrolysis resistant materials are used, it may be necessary to raise the temperature to upwards of 400° F. or more by increasing the pressure enough to prevent the water from changing to steam. Nevertheless, the presently preferred hydrolysis conditions which are sufficient for most materials are at a temperature of about 360° F. at a pressure of about 150 psi for a residency period of about 3 to 6 minutes.

The hydrolyzed slurry is neutralized at 74 to a preferably pH of about 4.5 to 5.0; preferable neutralizers 72 are sodium carbonate and sodium bicarbonate. This slightly acid slurry is properly called "wort," represented as 76 in FIG. 1, although colloquially it is referred to as "mash." The wort must be cooled to the fermentation temperature, which is preferably in the range of 88° F. to 90° F. According to the continuous manufacturing process of the present invention, it is advantageous to cool the wort in a series of cooling processes 78, thereby minimizing the amount of energy necessary.

For example, by discharging the wort into flash cooler 80, the temperature can be instantaneously lowered to about 260° F. to 220° F. It is preferable to then add yeast nutrients 82 to the wort because at this temperature, they are automatically sterilized and become completely mixed with the wort. Heating the yeast nutrients and the wort to a temperature in excess of 200° F. results in a significant advance over the prior art by preventing bacterial contamination of the fermentation vessels. The wort may then be pumped into a vacuum flash cooler 84, preferably a barometric condenser and ejector, where it is further cooled to a temperature of about 160° F. to 120° F. The wort is then pumped through cooler 86 where cooling water is added to bring the solution down to the fermentation temperature and the pH is adjusted to about 4.5 to 5.0. At this point, the wort is ready for fermentation process 90.

It will be appreciated the processes disclosed for delignifying and hydrolyzing the cellulosic materials described above are relatively severe since a strong acid or base is necessary in order to separate the lignin and cellulose. Moreover, these delignification processes require expensive equipment in order to recycle the acid, base, and methanol reagents. Such recycling equipment can amount to upwards of 40% of the total equipment costs for the alcohol manufacturing process; further, the operation of this recycling equipment can utilize up to 60% of the energy requirements of the entire manufacturing process.

An alternative to the above-described delignification processes which avoids the use of acids or bases has been discovered. It has been found that when cellulosic materials are heated under pressure in the presence of steam to a temperature of about 400° F., the cellulose cells begin to soften, and that when such materials are heated to about 480° F., the cellulose becomes practically amorphous. At temperatures of about 400° F. and the correspondingly high pressure, the cellulosic cells will absorb water from the steam into the spaces between the cells and through the cell walls (because of pressure) into the cell. The result is that the cells become hydrated. By suddenly subjecting these hydrated cellulosic cells to atmospheric pressure, the water within and between the cells explosively expands thereby destroying the cellulosic crystalline structure and disrupting the lignin seal. The effect of the expanding water vapor as it is subjected to atmospheric pressure, which is comparable to "popcorn popping," is to readily expose the cellulose cell structure so that the cellulose can be readily hydrolyzed by acid in the subsequent hydrolysis process.

Figure 5:
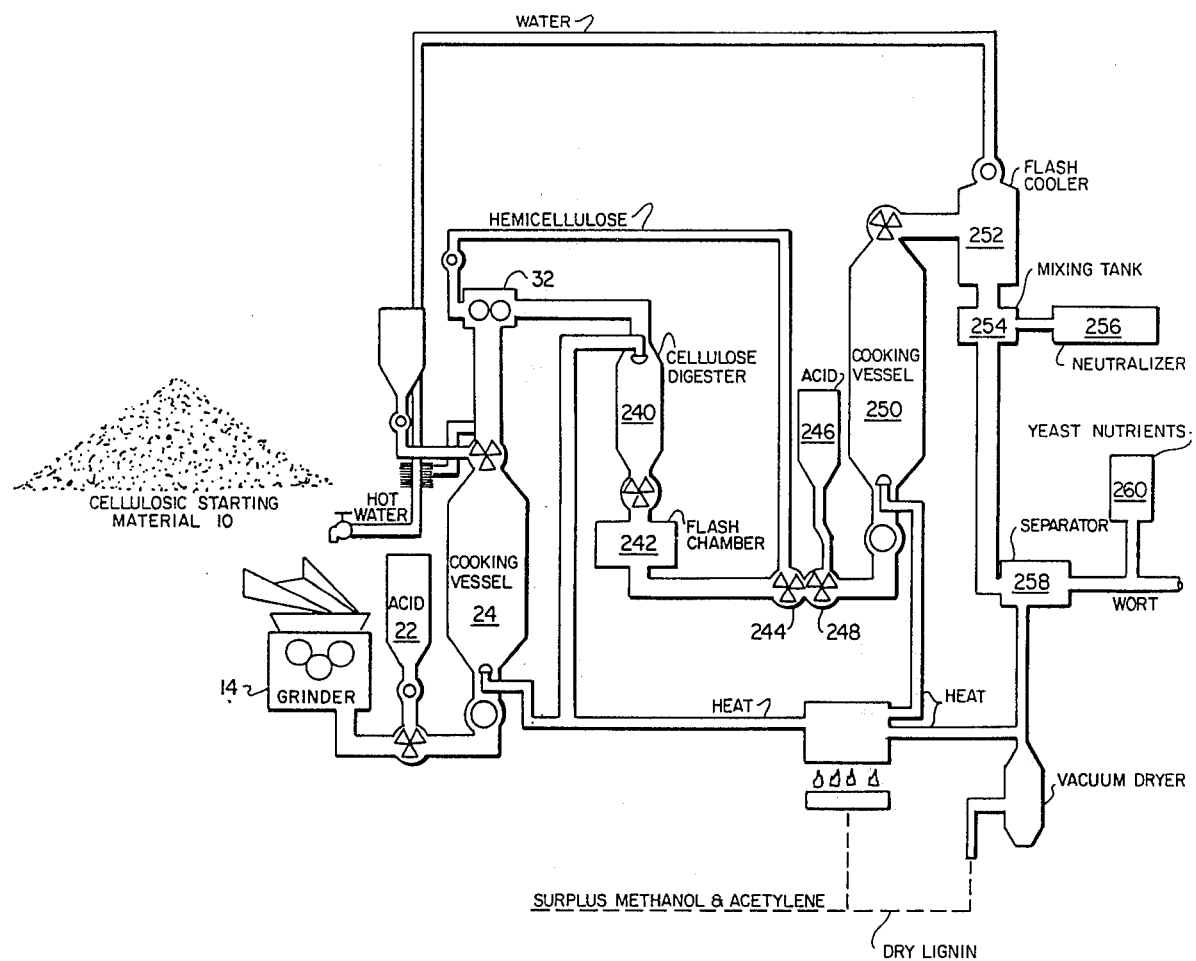
FIG. 5 is a schematic representation of an alternative embodiment of that portion of the continuous manufacturing process of the present invention depicted in FIG. 2 in which the cellulosic materials are converted into simple sugars in preparation for the fermentation process.

According to this method, which is illustrated in FIG. 5, the lignin and cellulose solids (from separator 32) are pumped into cellulose digester 240 which is maintained at a steam pressure of between about 250 and about 1500 psi (which, according to conventional steam tables, produces temperatures of about 400° F. to about 600° F.) for a period of about 3 to 30 minutes. The preferred conditions are about 700 psi (corresponding to about 500° F.) for about 10 to 15 minutes. Pressures of about 600 to 700 psi are required in order for the cells to become sufficiently hydrated to undergo the "popcorn popping" effect when the hydrated cells are subjected to atmospheric pressure. In addition, it is desirable to minimize the temperature to which the cellulosic materials are subjected because too high of temperature can char or scorch the cellulose. Accordingly, it will be appreciated that the effective use of the "popcorn popping" method is limited to relatively narrow pressure and temperature ranges. Of course, the time required to hydrate the cellulosic cells will vary depending upon the type of feedstock which is used. In addition, surfactants, such as 4X fire water, can be used to reduce the surface tension of the water molecules, thereby allowing for a more rapid hydration of the cellulose materials and a corresponding reduction in the residency time.

The hydrated materials are then ejected into flash chamber 242 which is maintained near atmospheric pressure. The sudden transfer of the hydrated cellulosic materials from a pressure of from about 250 psi to 1500 psi to atmospheric pressure results in disrupting of the lignin and exposing the cellulosic cell. Unlike the delignification processes using strong acid or base (discussed above) in which the cellulose is dissolved, the "popcorn popper" process does not separate the lignin and cellulose, but merely exposes the cellulose so that it can be readily hydrolyzed.

In preparation for hydrolysis, the resultant slurry (as it leaves flash chamber 242) is combined at 244 with hemicellulose 34. This slurry is then mixed with acid 246, preferably sulfuric acid, to a concentration of from about 0.5 to about 10 percent in continuous mixing tank 248, preferably about 0.5 percent. The slurry is hydrolyzed in cooking vessel 250 under the same conditions discussed with respect to the hydrolysis in cooking vessel 68 of FIG. 2. The cellulose is easily hydrolyzed under such conditions while the lignin remains uneffected by the acid at the described pressures and temperatures.

The hydrolyzed slurry is cooled through discharge into flash cooler 252. The slurry is then neutralized at 254 with neutralizer 256. At this point in the process, the sugars and are in solution, while the lignin, any undissolved cellulose, and other nonhydrolyzable components of the feedstock (such as plastic or other complex molecules which may be present in feedstocks such as garbage) are solids. These solids can be easily separated at 258, dried, then utilized as previously described. Although any type of conventional separation technique may be used, a convenient method of separating the solid from the fermentable sugars (or "wort") is the use of a vacuum filter belt which draws the solution from solids by use of a vacuum. A distinct advantage of a vacuum filter belt is that it simultaneously sufficiently cools the solution prior to fermentation without the use of coolers 84 and 86 (shown in FIG. 2). After yeast nutrients 260 are added to the sugar-containing solution (i.e., wort) and any minor changes in the temperature of pH of the solution is made, the solution is ready for fermentation.

It is particularly noteworthy that the wort prepared from cellulosic materials according to the processes of the present invention contains a very high proportion of simple sugars that are readily fermentable. Hence, nearly all of the sugars are converted in the fermentation process. Furthermore, unlike prior art processes, there is no need to add malt enzymes to the wort in order to convert the dextrins into fermentable sugars.

Figure 4:
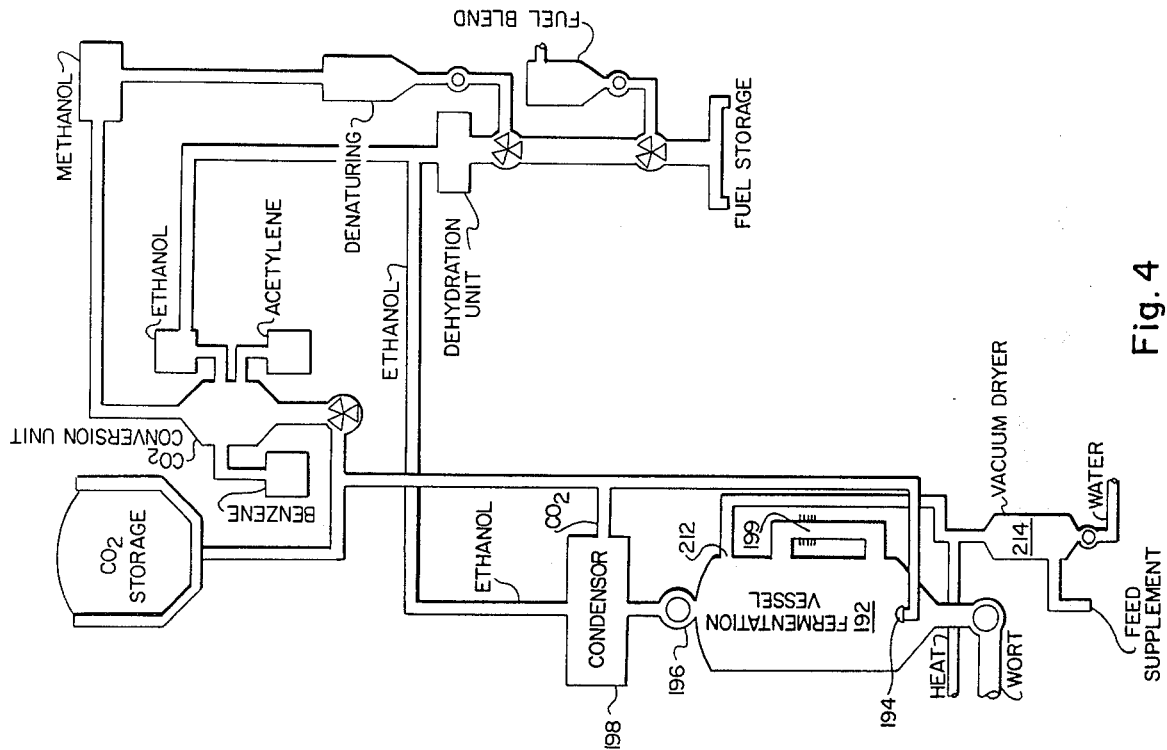
FIG. 4 is a schematic representation of an alternative embodiment of that portion of the continuous manufacturing process of the present invention depicted in FIG. 3.
Figure 3:
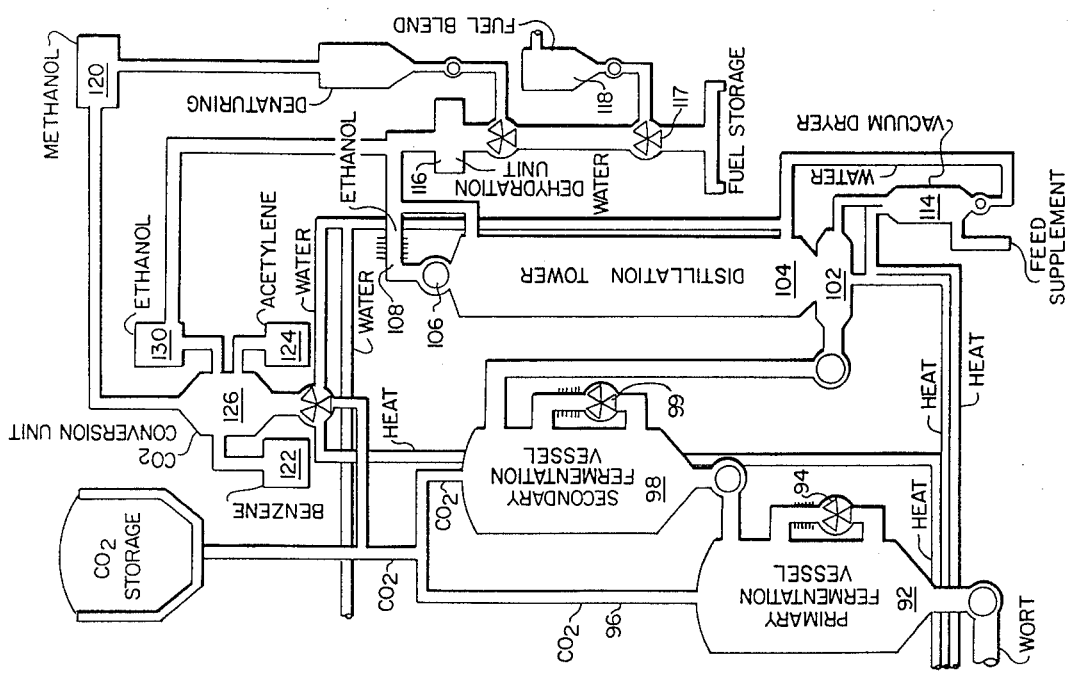
FIG. 3 is a schematic representation of an embodiment of a portion of the continuous manufacturing process of the present invention in which the simple sugars are fermented to ethanol and carbon dioxide and each is processed into final products.
Figure 6:
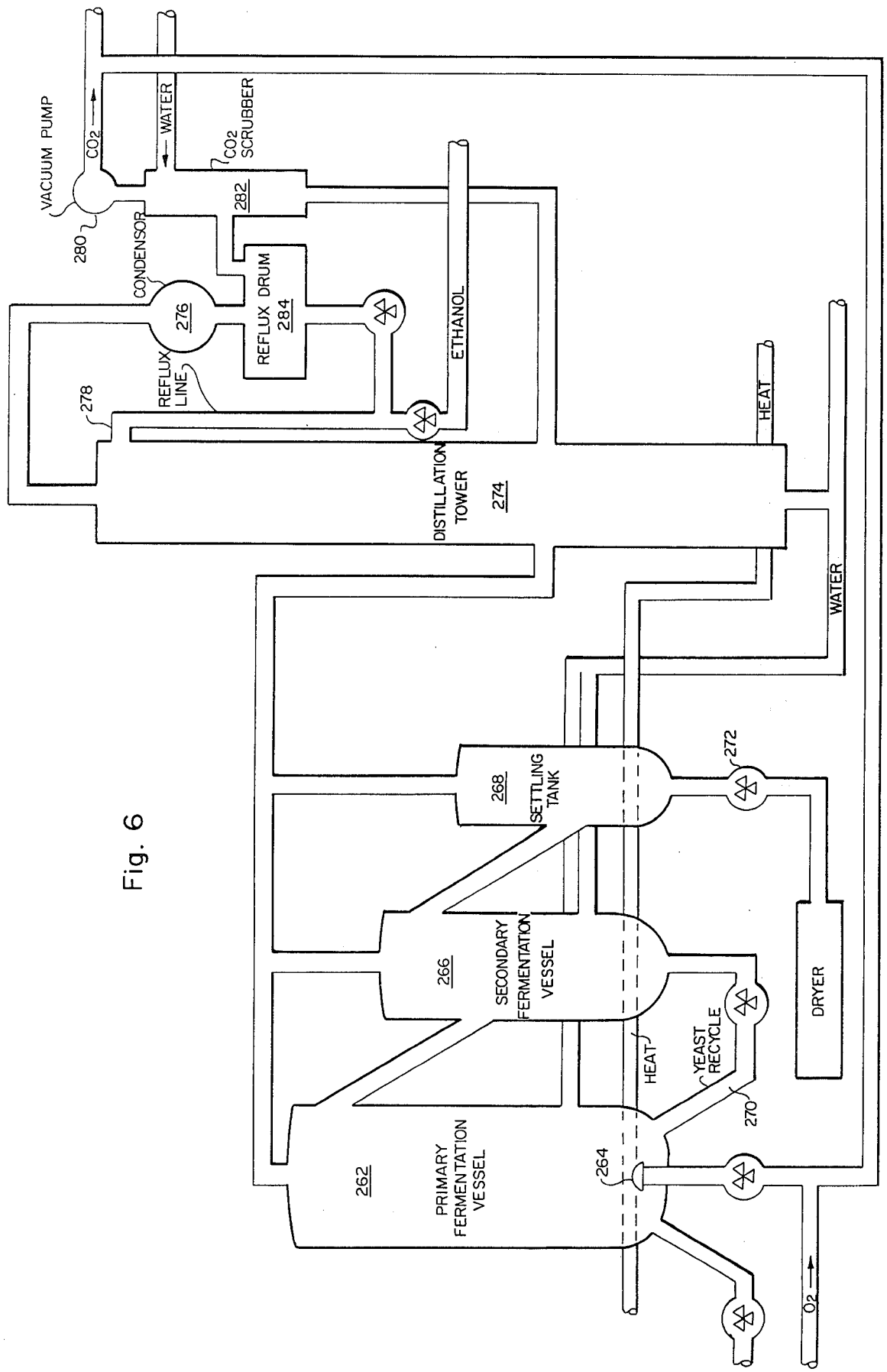
FIG. 6 is a schematic representation of an alternative embodiment of that portion of the continuous manufacturing process of the present invention depicted in FIGS. 3 and 4.

The present invention includes three alternative methods by which the sugars of the wort are fermented to alcohol and the alcohol is purified. These alternative methods are illustrated in FIGS. 3, 4 and 6 and are hereinafter separately discussed. According to the first method which is shown in FIG. 3, the wort (which has been cooled to about 88° F. to 90° F., which has had the pH adjusted to about 4.5 to 5.0, and which has been diluted with water to a concentration of about 15 percent to 25 percent sugar by weight) is pumped into the primary fermentation vessel 92 where it has a residency time of from about 6 hours to 11 hours, but preferably about 8 hours. Vessel 92 is provided with agitator means 94 which is preferably equipped with means capable of maintaining the solution of the wort within the preferable fermentation temperature range. Since the fermentation process is exothermic, means must be provided for cooling the solution as needed; also, if the environment outside of vessel 92 is cold, means must be provided for heating the solution to maintain the fermentation temperature.

Periodically (such as at the beginning of each startup cycle), sufficient yeast (preferably brewers yeast), generally represented as 88 in FIG. 1, is added to the primary fermentation vessel to bring the yeast cell count up to a concentration of about 100 million cells per milliliter in four hours. It has been found that under the conditions of the present invention, yeast is continuously propagated during the fermentation at a rate sufficient to maintain this optimum population.

As the wort undergoes fermentation, ethanol and carbon dioxide are produced in relative percentages of about 51 percent to 49 percent, respectively. Unlike the batch system of the prior art where the carbon dioxide is allowed to escape into the atmosphere or merely collected for sale as a byproduct, it has been found advantageous to utilize this produced carbon dioxide, represented as 96, for conversion to other useful products, discussed hereinafter.

Primary fermentation vessel 92 preferably has a constant level overflow to a secondary fermentation vessel 92 for an additional fermentation residency time of about 2 hours to 5 hours, preferably about 3 hours. Although it is within the scope of the present invention to only have one fermentation vessel where the residency time is adjusted accordingly, it has been found advantageous to utilize such as secondary fermentation vessel as it aids in achieving nearly complete fermentation of the sugars in the wort. Such an arrangement also allows any slower fermenting sugars to remain in the fermentation vessels for a longer time in order to complete the fermentation process. This is accomplished because the specific gravity of ethanol (approximately 1.0) is less than that of the wort (approximately 1.16 depending upon the sugar content); hence, the ethanol tends to rise to the top and move to the subsequent processing steps more quickly. Secondary fermentation vessel 98 is also provided with agitator and means 99 in order to maintain the proper fermentation temperature.

Accordingly, the total fermentation time is approximately 8 to 15 hours, preferably about 11 hours.

From the secondary fermentation vessel, the ethanol-containing wash is pumped to the distillation system, generally represented as 100, where it is heated in heater 102 which is located in the base of the distillation tower 104. By utilizing the heated vapors from the distillation tower, heater 102 can economically raise the temperature of the wash to be distilled.

One of the unique features of the present invention is the high temperature, low pressure operation of the distillation tower. By placing vacuum pump 106 at the top of distillation tower 104, the pressure within the tower is reduced. Although vacuum distillation has been utilized in the synthetic vitamin industry, such uses were at very low temperatures in order to protect the vitamins from degradation. However, in the present process, it is desirable to heat the ethanol-containing wash as hot as possible, preferably in the range of about 90° F. to 180° F., so that it will quickly vaporize within the distillation tower. It will be appreciated that the temperature of the ethanol-containing wash will be above the boiling point of ethanol at the pressures in the distillation tower, which pressures are kept as low as possible, preferably about 2 psi to 10 psi. This hybrid system of high temperature, low pressure allows for greater separation of the ethanol than conventional distillation towers or low-temperature vacuum distillation towers.

The effectivenes of any distillation tower is determined by its ability to make a rapid exchange of the components between the liquid and vapor phases, which is function of the vapor-liquid interfacial area and the flow characteristics of the vapor. The high temperature, low pressure system increases the velocity of the vapor traveling upward, thereby increasing the interphase transfer between liquid and vapor and resulting in an increased stripping action of the distillation tower. Hence, as part of the vapors condense and fall down the tower, the collision force is much greater than in conventional towers. At the same time, the vacuum changes the total pressure thereby making the separation easier because the relative volatility of the components of the solution is changed. Of course, care must be taken so that the upward forces of the vacuum are not so great as to create a lift on the liquid droplets which is greater than the gravity forces on the droplets.

Although it will be appreciated that a variety of conventional distillation towers will perform adequately according to the present invention, for illustrative purposes, one embodiment will be discussed. The ethanol-containing wash is pumped into the base of a distillation tower three feet in diameter and forty-eight feet high in which the lower section serves as a stripping section with about twenty perforated plates and the upper section as a rectifying column with about twenty-six bubble cap plates. Because of the reduced pressure under which the distillation is accomplished, a large cross-sectional area is preferred so that upward movement of the vapor is not inhibited by the expansion of the vapor caused by the reduced pressure. Otherwise, the capacity of the distillation tower is greatly reduced. Steam is sparged into the entering wash at about 3 psi thereby heating the solution to its boiling point. Accordingly, the ethanol is immediately vaporized upon entering the distillation tower.

Vacuum pump 106 reduces the pressure at the top of the distillation tower by preferably 20 psi to 30 psi. This results in a vapor rich in ethanol rapidly rising through the tower. As the vapor is drawn up the tower, it collides with droplets of water and ethanol which have condensed, resulting in a stripping action whereby the water is generally returned to the bottom of the distillation tower and the ethanol is generally drawn to the exit at the top of the tower. When the vapor exists at the top of the tower, it is easily condensed by cooling at 108.

Preferably, a portion of distillate 110 is returned to the tower as reflux to increase the stripping action and to control the proof of the distillate. The remainder of the ethanol distillate is sent to final processing 112. By controlling the amount of distillate which is returned to the tower, the concentration of the resulting ethanol product can be controlled. For instance, by allowing a larger portion of the distillate to return to the tower, the refluxing action is increased so that the distillate obtains a higher ethanol concentration. Concentrations of approximately 95 percent (190 proof) ethanol can be obtained. Should concentrations of only 140 or 150 proof be needed, such as in a blended ethanol-based fuel, a lesser amount of the distillate is returned to the tower.

The undistilled components or residues of the wash which remain in the bottom of the distillation tower can be continuously removed and dried, such as in vacuum dryer 114. When the starting cellulosic materials are forestry or other crop materials the dried residue can be used as a supplement to animal feeds or as a fertilizer. When the starting cellulosic materials are urban and industrial wastes, the dried residue can be used as fuel for heating plant or as a fertilizer.

The second method of the present invention by which the sugars are fermented to alcohol and the alcohol is purified eliminates the need for conventional distillation apparatus. It will be appreciated that the elimination of the conventional distillation tower in the ethanol manufacturing process is significant since the tower may represent a significant percent of the total capital investment required for building such an ethanol manufacturing plant and has one of the highest energy consumptions of any component in the manufacturing process. This alternate embodiment of the fermentation process, generally represented as 190 (in FIG. 1), is schematically depicted in FIG. 4. The wort is pumped into fermentation vessel 192 under the same temperature conditions discussed hereinbefore. The major difference is that a portion of the carbon dioxide which is produced by the fermentation process is recycled to the bottom of the fermentation vessel and sparged throughout the wort in the fermentation vessel. (Of course, other gases which do not inhibit the fermentation process may be used.) This pressurized sparging of finely divided carbon dioxide through jet 194 into the fermentation vessel will carry a mixture of ethanol and water from the fermented solution in vapor form. The preferred rate of carbon dioxide flow has been found to be about 0.01 cubic feet per minute to 0.5 cubic feet per minute per gallon of solution in the fermentation vessel. By putting the fermentation vessel under a slightly reduced pressure (lowering the pressure by up to 5 psi), such as by vacuum pump 196, the carbon dioxide will carry a richer ethanol mixture out of the vessel where it can be condensed and removed from the carbon dioxide in condensor 198. The ethanol which is about 190 proof can then be sent to final processing without the need for any further distillation.

It will be appreciated that the sparging carbon dioxide will use the collision with the fermentation solution (like the plates in the distillation tower) to strip away the ethanol for which carbon dioxide has an affinity. It is preferable that the carbon dioxide sparge be finely divided and be spread out so as to make contact with nearly all of the wort in the fermentation vessel. This can be accomplished by using any suitable sparge head, preferably a carbon or aloxite sparge head. Although it is preferable to have a temperature control means 200 to maintain the temperature of the fermentation solution, it is not necessary to also have an agitator means because the sparging carbon dioxide will provide sufficient agitation.

The nonethanol portions of the fermented solution including the dead yeast cells are gradually removed from the fermentation vessel through overflow 212 at the top of fermentation vessel 192, dried (such as in vacuum dryer 214), and used as a supplement to animal feed, as a fuel, or as a fertilizer.

The ethanol, whether it is condensed as it leaves distillation tower 104 (FIG. 3) or as it leaves fermentation vessel 192 (FIG. 4), is sent to final processing 112 where it may be dehydrated at 116 by benzene distillation or salt dehydration, may be denatured with methanol 120 or other approved formulas according to law, and/or may be stored. The ethanol may also be blended at 117 with other components, generally represented as 118, to make an ethanol-based fuel, such as that disclosed in copending United States application Ser. No. 087,618 filed Oct. 23, 1979.

The third method of the present invention by which the sugars are fermented to alcohol and the alcohol is purified is directed to removing the ethanol from the wort and distillating it to legally anhydrous purity. As illustrated in FIG. 6, the wort is pumped into primary fermentation vessel 262 where it has a residency time of between about 3 to 6 hours, but preferably about 4 hours. Even though the residency time is very short, as compared to prior art methods (and the other methods of the present invention), most of the sugars are completely fermented within that time period because, under the conditions outlined below, it is possible to maintain a population of up to 500 million yeast cells per milliliter. The significance of this advance in the art becomes clear in light of the fact that prior art processes typically only allow for a population of at most about 70 to 100 million yeast cells per milliliter.

One of the reasons that so high of a yeast population can be maintained is that the ethanol which is produced by fermentation is continuously removed from fermentation vessel 162. Hence, there is no ethanol inhibition of the fermentation process. The ethanol is removed from the fermentation vessel by continuously pulling a vacuum of about 20 to 26 inches of mercury, preferably about 25 inches. Moreover, carbon dioxide is sparged at 264 through the fermenting wort to aid the carrying off of the ethanol from the fermenting wort. (Small amounts of oxygen are also sparged through the fermenting wort to help maintain the yeast population.) By minimizing the ethanol concentration in vessel 262, it has been found that sugar solutions even as high as 40 and 50 percent can be used in the fermenting process, as compared to prior art processes which are generally limited to sugar solutions of less than 10 to 20 percent.

It will be appreciated that it may be necessary to add heat to the primary fermentation vessel because the constant evaporation of the ethanol from the wort would otherwise quickly drop the temperature below the preferred fermentation temperature. As indicated, most of the sugars are fermented while the wort is primary fermentation vessel 262. Nevertheless, there is a constant overflow into secondary fermentation vessel 266 where the final amounts of sugar are fermented and the ethanol is drawn off under vacuum. The secondary fermentation vessel also serves as a recycling station because the dead yeast cells (which float) tend to migrate to the top of the vessel where they ultimately overflow into settling tank 268. The live yeast cells become dormant with the diminishing food supply and sink to the bottom of vessel 266 where they are recycled at 270 to primary fermentation vessel 262. By returning the unspent yeast cells to the primary fermentation vessel, the high yeast cell concentration therein is maintained without the continuous addition of significant quantities of yeast. The solids which are collected in settling tank 268 are separated by a screw press 272 and dried. These solids make an excellent livestock feed supplement because they consist of proteins, heavy weight sugars, and other organic compounds.

As is depicted in FIG. 6, the ethanol vapor from fermentation vessels 262 and 264 is fed directly into distillation tower 274 in the vapor state. Experiments have shown that the ethanol (which is still in a vaporized state) is in a minimum concentration of about 15 to 20 percent when it enters the distillation tower. This is significant when compared to typical distillation towers when the ethanol only comprises about 4 to 10 percent of the liquid solution entering the tower and where the ethanol must be vaporized from a liquid solution once it has entered the distillation tower. Because the ethanol concentration is much greater (in the present invention) as it enters the distillation tower, less separation on the part of the tower will be required.

Vacuum pump 280 draws a vacuum in the distillation tower of about 20 to 26 inches of mercury, preferably about 25 inches of mercury. This greatly reduced pressure allows for a much greater separation of the ethanol. Moreover, the reduced pressure reduces the ethanol and water azeotrope so that the resulting product is about 99.6 percent ethanol (as compared to being able to obtain 95% ethanol at atmospheric pressure) with only one pass through the distillation tower. The resulting ethanol thus meets the legal requirements of 99.3% for anhydrous ethanol without the need for expensive benzene distillation procedures or the like. It has been found that with the ethanol entering the distillation tower in a vapor state and a reduced pressure of about 25 inches of mercury, the temperature at the bottom of the tower is about 110° F. and the temperature midway up the distillation tower is about 90° F.

The ethanol coming off of distillation tower 274 is liquidified by condenser 276. Some of the ethanol is passed through reflux drum 284 and then recycled back to the distillation tower at 278 in order to increase the efficiency of the tower. The carbon dioxide which is separated from the ethanol by the reflux drain contains a small percentage of ethanol. Accordingly, it is preferable to pass this vapor through scrubber 282 so that this ethanol can be ultimately collected.

A significant feature of the present invention is that a single vacuum source 280 is used to remove the ethanol from the wort in fermentation tanks 262 and 266 and to distill the ethanol in tower 274. This design allows for the maintaining of a lower ethanol concentration in the fermentation vessels while keeping the concentration of the vaporized ethanol entering the distillation tower relatively high, thereby minimizing the amount of separation which must be accomplished by the distillation tower.

It will be noted that condensor 276 is placed in the vacuum line between the distillation tower 274 and the vacuum pump 280. With this orientation, it is much easier to maintain the required vacuum because as the ethanol condenses at 276, it increases the vacuum pull on the distillation tower. If it were not for the fact that the vacuum was being used to remove the ethanol from the fermentation tanks, it would be necessary to bleed a gas into the distillation tower to prevent collapsing of the tower. However, because of the coordinated arrangement of the vacuum system (including the vacuum pump and the condensor) with both the distillation tower and the fermentation tanks, the power requirements are greatly reduced.

One of the important features of the present invention is its versatility in accomodating a variety of starting materials. Accordingly, as the available starting materials vary over a period of time or several different types of starting materials become available, no significant modification need be made to the process of the present invention. For example, if a source of pulped cellulose were available at any given time, it could simply be added into the process before the cadoxen or concentrated acid step of the delignification process, such as through valve 140 depicted in FIG. 2. If a source of starch materials were available, materials could be added just before the acid hydrolysis, such as through valve 142. If starting materials containing simple sugars were available, they might be added to the continuous process at a point just before the fermentation process, such as through valve 144, which would subject the materials to a temperature high enough to sterilize them.

Another of the features of the present invention is to utilize all of the byproducts. Accordingly, methanol 120 for denaturing and the major components of a blended ethanol-based fuel, benzene 122 and acetylene 124, can be synthetically manufactured in carbon dioxide conversion unit 126 from the excess carbon dioxide produced as a byproduct of the fermentation process. Moreover, additional quantities of ethanol can be synthetically produced from the excess carbon dioxide. The process of producing this synthetic ethanol 130 utilizes the heretofore wasted carbon dioxide byproduct of the fermentation process to dramatically increase the yield of ethanol. In fact, without increasing the amount of starting cellulosic materials or the size or number of the processing vessels or distillation towers, it is possible to nearly double the production of ethanol.

The following processes, which are individually known in the prior art, are demonstrative of the uses to which the carbon dioxide may be put. While many processes for converting carbon dioxide to basic chemicals are known, the present invention is unique in its use of carbon dioxide as the basic raw material for the production of essential petrochemicals. It will be appreciated that the resultant products discussed hereinafter, as well as others which could be produced according to present technology, are the basic materials and feedstocks for the current petrochemical industry. The present invention utilizes the interrelatedness of the many basic raw materials in the petrochemical industry.

For example, carbon dioxide from the fermentation vessels can be reacted with carbon at elevated temperatures (such as about 600° C. to 1000° C.) to produce carbon monoxide:

$$C + CO_2 \rightarrow 2CO$$

Such a process is currently used in the steel industry.

Carbon monoxide can be reacted with water at temperatures of about 200° C. to 500° C. to form hydrogen and carbon dioxide:

$$CO + H_2O \rightarrow CO_2 + H_2$$

This process is often used with coal and coke gasification. With the components supplied from these two basic reactions (carbon dioxide, carbon monoxide, and hydrogen), many important petrochemicals can be made.

For instance, carbon monoxide and hydrogen in the presence of a variety of well-known mixed metal oxide catalysts can be combined at temperatures of about 300° C. to 600° C. and pressures of about 100 to 200 atmospheres to produce both methanol and benzene:

$$CO + 2H_2 \rightarrow CH_3OH$$

$$12CO + 3H_2 \rightarrow C_6H_6 + 6CO_2$$

Methanol can also be produced by the well-known Fisher-Tropsch process.

Additionally, carbon monoxide can be combined with methane (which can be made from carbon monoxide and hydrogen, anaerobic digestion, or natural gas) and water at temperatures of about 300° C. to 600° C. over iron catalysts to yield ethanol and iron oxide:

$$CO + CH_4 + H_2O \rightarrow C_2H_5OH + \text{iron oxide}$$

It is through this type of synthetic production of ethanol that allows for greater production quantities of ethanol without increasing the amount of cellulosic starting materials. Also, acetylene can be produced from methane with a low electric discharge, and ethylene, a basic chemical in the petrochemical industry, can be produced.

It is evident from the foregoing that to fully utilize the carbon dioxide byproduct will not only provide the chemicals necessary to the preparation of an ethanol-based fuel, but also other chemicals which may be useful directly or as intermediates in the petrochemical industry.

It will be appreciated that the described continuous ethanol manufacturing process allows for maximization of the efficiency of each step in the overall process. For example, in the prior art batch methods, it was necessary to conduct several operations in the same cooking vessel; however, according to the present invention, each processing step can be conducted in a vessel specially designed for each operation and at the temperature and pressure conditions most suited for that operation. By conducting each operation at the optimum conditions, the yield of ethanol can be greatly improved.

Moreover, it is not necessary according to the present invention to use the large cooking (about 10,000–13,000 gallons) and fermentation (about 500,000 gallons) vessels of the prior art which occupy considerable floor space. It will be appreciated that such large vessels are not energy efficient in the heating or pressurization steps and are not condusive to obtaining and maintaining uniform conditions of mixing and temperature—such uniform conditions are particularly critical during the fermentation process. Such large vessels also result in long time lags in heating and cooling the large quantities of solutions.

One of the most significant advantages of the present invention is that the fermentation time is dramatically reduced from about 72 hours to a total about three to six hours. This reduction is possible because of the high yeast population and the minimizing of ethanol inhibition. Because there is a constant flow of wort into the fermentation vessel and ethanol out of the vessel, there is a continuous propogation of yeast during the fermentation process which maintains an optimum population.

In view of the foregoing, it will be appreciated that the present invention may be embodied in many specific forms and in specific embodiments which are not exemplified above, without departing from the spirit or essential characteristics of the present invention. The described embodiment is to be considered in all respects only as illustrative and not restrictive and the scope of the invention is, therefore, indicated by the appended claims rather than the foregoing description. All variations which come within the meaning and range of equivalency of the claims are to be embraced within their scope.

What is claimed to be secured by United States Letters Patent is:

1. A process for the production of alcohol from cellulosic material, the process consisting essentially of:
   obtaining a feedstock, at least a portion of which is a cellulosic material;
   pressurizing the feedstock with steam to a first pressure within the range of about 250 psi to about 1500 psi at a temperature within the range of about 400° F. to about 600° F. for a period of between about three and about thirty minutes;
   disrupting the internal structure of at least a portion of the cellulosic material by subjecting said cellulosic material to a substantially reduced second pressure, the disrupted cellulosic material being readily hydrolyzable into fermentable sugars;
   hydrolyzing the disrupted cellulosic material with a first dilute acid solution to produce fermentable sugars;
   fermenting the fermentable sugars to produce alcohol; and
   concentrating the alcohol by passing the alcohol through a distillation column.

2. A process as defined in claim 1 wherein the cellulosic material is a waste material selected from the group consisting of corn residue, forestry, feedlot, crop, urban, or industrial wastes.

3. A process as defined in claim 1 wherein said feedstock is pressurized with steam to a first pressure within the range of about 600 psi to about 800 psi at a temperature within the range of about 480° F. to about 520° F. for a period of about ten to about fifteen minutes.

4. A process as defined in claim 1 further comprising the steps of:
   dissolving at least a portion of the cellulosic material in the feedstock with a second dilute acid solution before the pressurizing step, thereby producing a solution comprising hemicellulose; and
   separating the solution from undissolved cellulosic material remaining in the feedstock in preparation for pressurizing the feedstock with steam.

5. A process as defined in claim 4 wherein the concentration of the second dilute acid solution in which said hemicellulose is dissolved is from about 0.5% to about 2.0% acid by volume.

6. A process as defined in claim 5 wherein the acid of the second dilute acid solution is sulfuric acid.

7. A process as defined in claim 5 wherein the cellulosic material and the second dilute acid solution are heated to a temperature within the range of about 200° F. to about 300° F. at a pressure of about 5 psi to about 50 psi for a period of about two minutes to about ten minutes.

8. A process as defined in claim 4 further comprising the step of hydrolyzing the hemicellulose together with the disrupted cellulosic material using the first dilute acid solution, thereby producing fermentable sugars.

9. A process as defined in claim 8 wherein the first dilute acid solution by which the hemicellulose and disrupted cellulosic material are hydrolyzed into fermentable sugars is in an acid concentration by volume of about 0.5% to about 10%.

10. A process as defined in claim 9 wherein the acid of said first dilute acid solution is sulfuric acid.

11. A process as defined in claim 9 wherein the disrupted cellulosic material and the hemicellulose are hydrolyzed at a temperature within a range of about 200° F. to about 400° F. at a pressure from about 15 psi to about 200 psi for a period of about two minutes to about ten minutes.

12. A process as defined in claim 1 wherein the acid of the first dilute acid solution is sulfuric acid.

13. A process as defined in claim 1 wherein said second pressure is about atmospheric pressure.

14. A process for the production of alcohol from cellulosic material, the process comprising:
   obtaining a feedstock, at least a portion of which is a cellulosic material;
   dissolving at least a portion of the cellulosic material with a first dilute sulfuric acid solution having a concentration by volume of about 0.5% to about 2.0% at a temperature within the range of about 200° F. to about 300° F. at a pressure of about 5 psi to about 50 psi for a period of about two minutes to about ten minutes, thereby producing a first solution comprising hemicellulose;
   separating the first solution from undissolved cellulosic material;
   pressurizing the undissolved cellulosic material with steam to a first pressure within the range of about 250 psi to about 1500 psi at a temperature within the range of about 400° F. to about 600° F. for a period of about three to about thirty minutes;
   disrupting the internal structure of the undissolved cellulosic material by subjecting said undissolved cellulosic material to a substantially reduced second pressure, the disrupted cellulosic material being readily hydrolyzable into fermentable sugars;
   hydrolyzing the hemicellulose from the first solution and the disrupted cellulosic material with a second dilute sulfuric acid solution having a concentration of about 0.5% to about 10% acid by volume at a temperature of about 200° F. to about 400° F. at a pressure from about 15 psi to about 200 psi for a period of about two minutes to about ten minutes, thereby producing fermentable sugars;
   fermenting the fermentable sugars to produce alcohol; and
   concentrating the alcohol by passing the alcohol through a distillation column.

15. A process for the production of alcohol from cellulosic material, the process comprising:
  obtaining a feedstock, at least a portion of which is a cellulosic material;
  dissolving at least a portion of the cellulosic material with a first dilute acid solution, thereby producing a first solution comprising hemicellulose;
  separating the first solution from undissolved cellulosic material;
  pressurizing the undissolved cellulosic material with steam to a first pressure within the range of about 250 psi to about 1500 psi at a temperature within the range of abut 400° F. to about 600° F. for a period of about three to about thirty minutes;
  disrupting internal structure of the undissolved cellulosic material by subjecting said undissolved cellulosic material to a substantially reduced second pressure, the disrupted cellulosic material being readily hydrolyzable into fermentable sugars;
  hydrolyzing with a second dilute acid solution the hemicellulose from the first solution and the disrupted cellulosic material, thereby producing fermentable sugars;
  introducing fermentable sugars into a fermenter;
  mixing yeast with the fermentable sugars and fermenting the fermentable sugars to produce alcohol and carbon dioxide;
  removing alcohol vapor and carbon dioxide from the fermenter under a partial vacuum, said removal being aided by sparging a gas throughout the fermentable sugars in the fermenter at a rate of about 0.01 to about 0.5 cubic feet per minute per gallon of fermentable sugars in said fermenter;
  concentrating the alcohol vapor by passing the alcohol vapor and carbon dioxide through a distillation column under said partial vacuum while refluxing a liquid alcohol through the distillation column, said fermenter being in gaseous communication with said distillation column; and
  condensing said alcohol vapor which has passed through the distillation column, thereby producing liquid alcohol and thereby creating a portion of said partial vacuum.

16. A process for the production of alcohol from cellulosic material, comprising the steps of:
  obtaining a feed stock, at least a portion of which is a cellulosic material;
  pressurizing the feedstock with steam to a first pressure within the range of about 250 psi to about 1500 psi at a temperature within the range of about 400° F. to about 600° F. for a period of about three to about thirty minutes;
  disrupting the internal structure of at least a portion of the cellulosic material by subjecting said cellulosic material to a substantially reduced second pressure, said disrupted cellulosic material being substantially delignified so as to be readily hydrolyzable into fermentable sugars;
  hydrolyzing the disrupted cellulosic material into fermentable sugars;
  fermenting the fermentable sugars to produce alcohol; and
  concentrating the alcohol by passing the alcohol through a distillation column.

17. A process as defined in claim 16 wherein the disrupted cellulosic material is hydrolyzed with a dilute sulfuric acid solution, thereby producing fermentable sugars.

18. A process for the production of alcohol from cellulosic material, the process comprising:
  obtaining a feedstock, at least a portion of which is a cellulosic material;
  pressurizing the feedstock with steam to a first pressure within the range of about 250 psi to about 1500 psi at a temperature within a range of about 400° F. to about 600° F. for a period of about three to about thirty minutes;
  disrupting the internal structure of at least a portion of the cellulosic material by subjecting said cellulosic material to a substantially reduced second pressure, the disrupted cellulosic material being readily hydrolyzable into fermentable sugars;
  hydrolyzing the disrupted cellulosic material with a first dilute acid solution to produce fermentable sugars;
  introducing the fermentable sugars into a fermenter;
  mixing yeast with the fermentable sugars and fermenting the fermentable sugars to produce alcohol and carbon dioxide;
  removing alcohol vapor and carbon dioxide from the fermenter under a partial vacuum, said removal being aided by sparging a gas throughout the fermentable sugars in the fermenter at a rate of about 0.01 to about 0.5 cubic feet per minute per gallon of fermentable sugars in said fermenter;
  concentrating the alcohol vapor by passing the alcohol vapor and carbon dioxide through a distillation column under said partial vacuum while refluxing a liquid alcohol through the distillation column, said fermenter being in gaseous communication with said distillation column; and
  condensing said alcohol vapor which has passed through the distillation column, thereby producing liquid alcohol and thereby creating at least a portion of said partial vacuum.

19. A process as defined in claim 18 wherein the cellulosic material is a waste material selected from the group consisting of corn residue, forestry, feedlot, crop, urban, or industrial wastes.

20. A process as defined in claim 18 further comprising the steps of:
  dissolving at least a portion of the cellulosic material in the feedstock with a second dilute acid solution before the pressurizing step, thereby producing a solution comprising hemicellulose; and
  separating the solution from undissolved cellulosic material remaining in the feedstock in preparation for pressurizing the feedstock with steam.

21. A process as defined in claim 20 wherein the concentration of the second dilute acid solution in which said hemicellulose is dissolved is from about 0.5% to about 2.0% acid by volume.

22. A process as defined in claim 21 wherein the acid of the second dilute acid solution is sulfuric acid.

23. A process as defined in claim 21 wherein the cellulosic material and the second dilute acid solution are heated to a temperature within the range of about 200° F. to about 300° F. at a pressure of about 5 psi to about 50 psi for a period of about two minutes to about ten minutes.

24. A process as defined in claim 20 further comprising the step of hydrolyzing the hemicellulose together with the disrupted cellulosic material using the first dilute acid solution, thereby producing fermentable sugars.

25. A process as defined in claim 24 wherein the first dilute acid solution by which the hemicellulose and disrupted cellulosic material are hydrolyzed into fermentable sugars is in an acid concentration by volume of about 0.5% to about 10%.

26. A process as defined in claim 25 wherein the acid of said first dilute acid solution is sulfuric acid.

27. A process as defined in claim 25 wherein the disrupted cellulosic material and the hemicellulose are hydrolyzed at a temperature within the range of about 200° F. to about 400° F. at a pressure from about 15 psi to about 200 psi for a period of about two minutes to about ten minutes.

28. A process as defined in claim 18 wherein said second pressure is about atmospheric pressure.

29. A process as defined in claim 18 wherein said feedstock is pressurized with steam to a first pressure within the range of about 600 psi to about 800 psi at a temperature within the range of about 480° F. to about 520° F. for a period of about ten to about fifteen minutes.

* * * * *

UNITED STATES PATENT AND TRADEMARK OFFICE
CERTIFICATE OF CORRECTION

PATENT NO. : 4,425,433            Page 1 of 2
DATED : January 10, 1984
INVENTOR(S) : Alan M. Neves It is certified that error appears in the above—identified patent and that said Letters Patent is hereby corrected as shown below:

Column 2, line 18, "Furtermore" should be --Furthermore--

Column 6, line 22, (Table) "Tons/Year (x $^6$)" should be --Tons/Year (x$10^6$)--

Column 6, lines 26-32 (Table) should be arranged as follows:

| | |
|---|---|
| Cellulosic wastes: | 1,010 |
|     Corn residue | 140    (x $10^6$) |
|     Forestry | 200 |
|     Feedlot | 237 |
|     Bagasse | 10 |
|     Other cropwastes | 233 |
|     Urban | 130 |
|     Industrial | 60 |

UNITED STATES PATENT AND TRADEMARK OFFICE
CERTIFICATE OF CORRECTION

PATENT NO. : 4,425,433
DATED : January 10, 1984
INVENTOR(S) : Alan M. Neves

It is certified that error appears in the above—identified patent and that said Letters Patent is hereby corrected as shown below:

Column 11, lines 2-3, There should be no paragraph division here.

Column 11, line 3, "250" should be in regular, not boldface type

Column 11, line 51, delete "and"

Column 12, line 51, "92" should be --98--

Column 14, line 31, "plant" should be --plants--

Column 19, line 12, "propogation" should be --propagation--

Column 20, line 24, "a range" should be --the range--

Signed and Sealed this

Sixteenth Day of September 1986

[SEAL]

Attest:

DONALD J. QUIGG

Attesting Officer

Commissioner of Patents and Trademarks